(12) United States Patent
Singhatat

(10) Patent No.: US 9,918,663 B2
(45) Date of Patent: Mar. 20, 2018

(54) FEEDBACK WEARABLE

(71) Applicant: Wamis Singhatat, Malvern, PA (US)

(72) Inventor: Wamis Singhatat, Malvern, PA (US)

(*) Notice: Subject to any disclaimer, the term of this patent is extended or adjusted under 35 U.S.C. 154(b) by 0 days.

(21) Appl. No.: 15/350,698

(22) Filed: Nov. 14, 2016

(65) Prior Publication Data

US 2017/0135612 A1   May 18, 2017

Related U.S. Application Data

(60) Provisional application No. 62/255,473, filed on Nov. 15, 2015.

(51) Int. Cl.
*A61B 5/00* (2006.01)
*A61B 5/11* (2006.01)

(52) U.S. Cl.
CPC .......... *A61B 5/1117* (2013.01); *A61B 5/6814* (2013.01); *A61B 5/6831* (2013.01); *A61B 5/742* (2013.01); *A61B 5/7455* (2013.01); *A61B 2562/0219* (2013.01)

(58) Field of Classification Search
CPC .......................... A61B 5/1117; A61B 5/4023
See application file for complete search history.

(56) References Cited

U.S. PATENT DOCUMENTS

| | | | |
|---|---|---|---|
| 5,919,149 A * | 7/1999 | Allum | A61B 5/1116 600/595 |
| 7,292,151 B2 | 11/2007 | Ferguson et al. | |
| 7,815,516 B1 | 10/2010 | Mortimer et al. | |
| 7,915,790 B2 | 3/2011 | Heim et al. | |
| 8,040,223 B2 | 10/2011 | Mortimer et al. | |
| 8,072,121 B2 | 12/2011 | Heim et al. | |
| 8,092,355 B2 | 1/2012 | Mortimer et al. | |
| 8,219,909 B2 | 7/2012 | Hanlon et al. | |
| 8,398,569 B1 | 3/2013 | Mortimer et al. | |
| 8,427,325 B2 | 4/2013 | Ferguson et al. | |

(Continued)

FOREIGN PATENT DOCUMENTS

| | | |
|---|---|---|
| KR | 1020110053447 | 5/2011 |
| WO | WO-2004091400 A1 | 10/2004 |

OTHER PUBLICATIONS

International Search Report and Written Opinion for WO Application No. PCT/US/2016/061844, dated Feb. 24, 2017.

(Continued)

*Primary Examiner* — Michael C Stoudt
*Assistant Examiner* — Nicholas E Kolderman
(74) *Attorney, Agent, or Firm* — Honigman Miller Schwartz and Cohn LLP

(57) ABSTRACT

A method of operating a wearable includes receiving an inertial movement from an inertial measurement sensor disposed on a user. The inertial measurement is indicative of a movement of the user from a first pose to a second pose away from the first pose. The method also includes determining a movement vector defining the movement of the user from the first pose to the second pose based on the inertial measurement. The movement vector is relative to the first pose. The method also includes determining whether the movement vector satisfies a threshold movement vector. When the movement vector satisfies a threshold movement vector, the method includes instructing at least one actuator to apply a feedback response on the user.

29 Claims, 11 Drawing Sheets

(56) References Cited

U.S. PATENT DOCUMENTS

| | | | |
|---|---|---|---|
| 9,092,953 B1 | 7/2015 | Mortimer et al. | |
| 9,149,222 B1* | 10/2015 | Zets | A61B 5/16 |
| 9,367,136 B2 | 6/2016 | Latta et al. | |
| 2006/0022833 A1 | 2/2006 | Ferguson et al. | |
| 2006/0161079 A1 | 7/2006 | Choi et al. | |
| 2009/0023122 A1 | 1/2009 | Lieberman et al. | |
| 2010/0102677 A1 | 4/2010 | Heim et al. | |
| 2010/0256537 A1 | 10/2010 | Menga | |
| 2010/0286571 A1* | 11/2010 | Allum | A61B 5/1116 600/595 |
| 2011/0043537 A1 | 2/2011 | Dellon et al. | |
| 2011/0172743 A1* | 7/2011 | Davis | A61B 5/0031 607/62 |
| 2014/0260714 A1* | 9/2014 | Vallery | A61H 3/00 74/5.37 |
| 2015/0209212 A1 | 7/2015 | Duguid | |

OTHER PUBLICATIONS

Afzal et al., "Effects of kinesthetic haptic feedback on standing stability of young healthy subjects and stroke patients," Journal of NeuroEngineering and Rehabilitation, (2015) 12:27.

Beom-Chan Lee and Kathleen H. Sienko, Ph.D., "Balance Training Via Multimodal Biofeedback," Department of Mechanical Engineering, University of Michigan.

Rabin et al., "Haptic feedback from manual contact improves balance control in people with Parkinson's disease," National Institute of Health, Gait Posture. Jul. 2013; 38(3): 373-379.

Zong-Hao Ma et al., "A Vibrotactile and Plantar Force Measurement-Based Biofeedback System: Paving the Way towards Wearable Balance-Improving Devices," Sensors 2015, 15, 31709-31722.

Dr. Bruce Mortimer, "Applications and Approaches to Vibrotactile Feedback," Engineering Acoustics, Inc.

NeuroCom® Smart Balance Master®, "Objective Balance Assessment & Dynamic Training Protocols," Natus® Balance & Mobility, 2015.

* cited by examiner

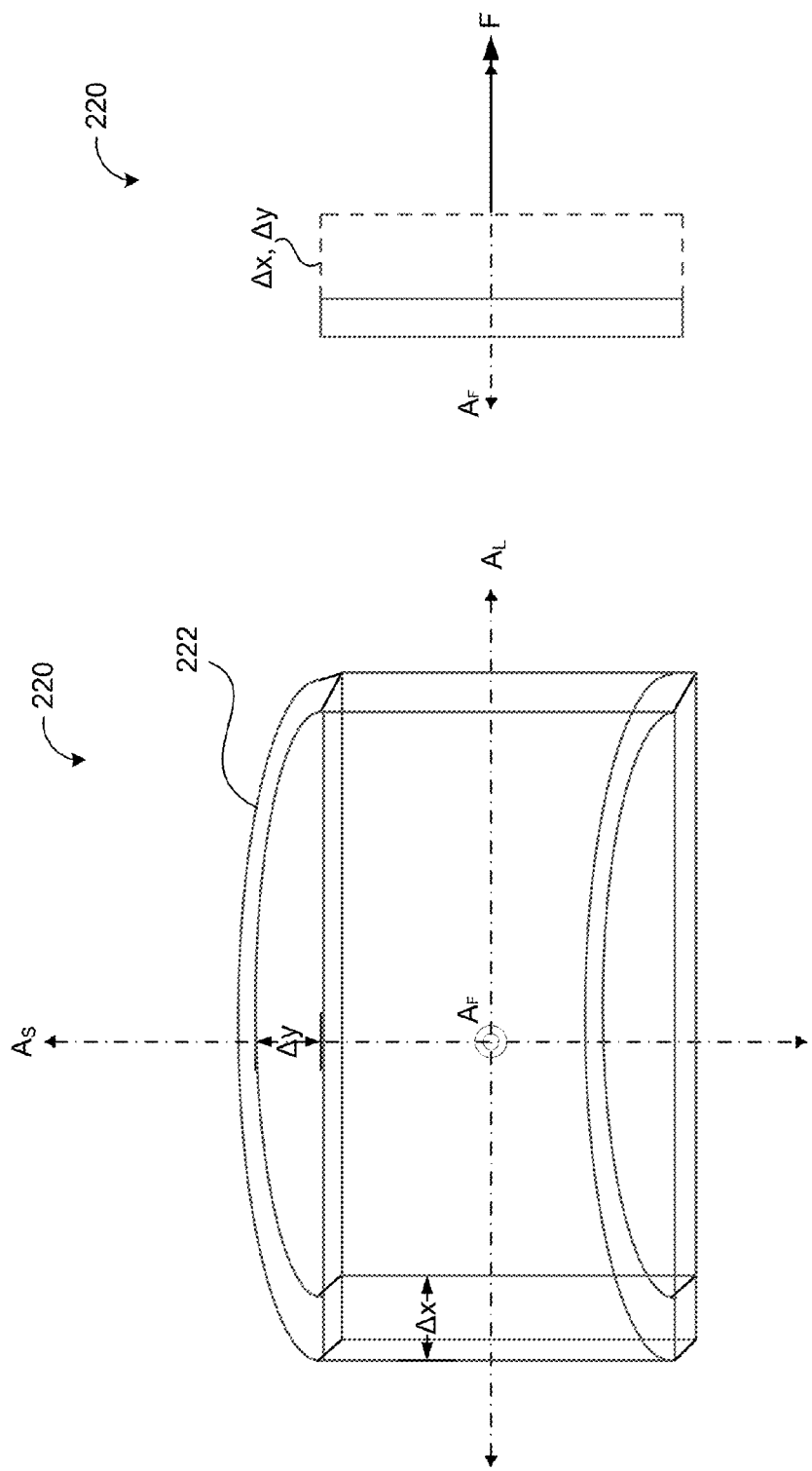

FEEDBACK WEARABLE

CROSS REFERENCE TO RELATED APPLICATIONS

This U.S. patent application claims priority under 35 U.S.C. § 119(e) to U.S. Provisional Application 62/255,473, filed on Nov. 15, 2015, which is hereby incorporated by reference in its entirety.

TECHNICAL FIELD

This disclosure relates to wearables that provide feedback responses to a user.

BACKGROUND

Falls are the leading cause of unintentional death from injury in those over 65 years of age in the U.S. and other developed countries. One out of three adults over the age of 65 falls every year, and half of these are from recurrent fallers. The causes of falls among the elderly are usually multi-factorial, and include both extrinsic and intrinsic factors. Extrinsic causes of falling include illumination, floor surface, furniture, and other environmental factors, and can often be addressed with proper education and precautions to minimize tripping and slipping hazards within the living environment. Intrinsic causes, on the other hand, include many factors such as medication side effects, neurological diseases, illnesses, infections, cognitive impairments, and the natural functional decline associated with aging, and as a result, can be more challenging to address. Various feedback approaches currently exist that include vibrotactile and gyroscope-based force actuators that aim to improve sensory and motor-control functions important in sensing and correcting imbalance of a user.

SUMMARY

A common by-product of many of the aforementioned intrinsic factors is an impaired ability for an older adult to appropriately sense and to correct balance. Current approaches to improve the ability for those with impaired balance are limited and mostly relegated to physical therapy that focuses on improving response to imbalance-inducing scenarios and/or strengthening core muscles involved in maintaining balance. These approaches, however, provide limited real-time feedback to older adults regarding their balance and thus do little to improve sensory and motor-control functions important to sensing and to adjust imbalance. The present disclosure provides systems and methods for sensing movement of a user and providing feedback to the user based on an identification of the movement of the user.

One aspect of the disclosure provides a method of operation for a wearable. The method includes receiving, at data processing hardware, an inertial movement from an inertial measurement sensor disposed on a user. The user defines a vertical gravitational axis and a forward travel direction. The user has a pose defined by a sway angle of the user relative to the vertical gravitational axis and a sway direction of the user relative to the forward travel direction. The inertial measurement is indicative of a movement of the user from a first pose to a second pose away from the first pose. The method also includes determining, by the data processing hardware, a movement vector defining the movement of the user from the first pose to the second pose based on the inertial measurement. The movement vector is relative to the first pose. The method also includes determining, by the data processing hardware, whether the movement vector satisfies a threshold movement vector. When the movement vector satisfies a threshold movement vector, the method includes instructing, by the data processing hardware, at least one actuator to apply a feedback response on the user.

Implementations of the disclosure may include one or more of the following optional features. In some implementations, determining whether the movement vector satisfies a threshold movement vector includes determining whether the movement vector extends beyond a movement envelope defined by a collection of envelope movement vectors relative to the vertical gravitational axis and the forward travel direction of the user at the first pose. The movement vector may include an angular displacement of the user from the first pose to the second pose. The movement vector may also include a horizontal translation relative to the vertical gravitational axis of the user from the first pose to the second pose.

In some examples, the user has a center of gravity and the vertical gravitational axis intersects the center of gravity of the user along a direction of gravity. The at least one inertial measurement sensor may include at least one of a tri-axial accelerometer, a tri-axial magnetometer, or a tri-axial gyroscope. The at least one actuator and the inertial measurement sensor may be disposed on a band wearable by the user. The at least one actuator may include at least one of an electro-mechanical polymer, a piezo-electric actuator, a solenoid actuator, a pneumatic actuator, a hydraulic actuator, or a linear actuator.

Instructing the at least one actuator to apply the feedback response on the user may include instructing a display of a stationary virtual object on an electronic display in communication with the data processing hardware. The feedback response may include at least one of a force at least partially opposite to and proportional to the movement vector, an audible signal, an emitted light, or a vibration.

Another aspect of the disclosure provides a wearable including a band, actuators disposed on the band, an inertial measurement sensor, and a controller. The actuators are circumferentially spaced along the band. Each actuator is configured to apply a force, such as a diametric force, to a user donning the band. The controller is in communication with the actuators and the inertial measurement sensor, and is configured to perform operations. The operations include receiving an inertial measurement from the inertial measurement sensor, determining a movement vector defining the movement of the user from the first pose to the second pose based on the inertial measurement, and determining whether the movement vector satisfies a threshold movement vector. The user defines a vertical gravitational axis and a forward travel direction. The user has a pose defined by a sway angle of the user relative to the vertical gravitational axis and a sway direction of the user relative to the forward travel direction. The inertial measurement is indicative of a movement of the user from a first pose to a second pose away from the first pose. The movement vector is relative to the first pose. When the movement vector satisfies a threshold movement vector, the operations include instructing at least one actuator to apply a force on the user. The force is at least partially opposite to and proportional to the movement vector.

This aspect may include one or more of the following optional features. In some implementations, determining whether the movement vector satisfies a threshold movement vector includes determining whether the movement vector extends beyond a movement envelope defined by a collection of envelope movement vectors relative to the vertical gravitational axis and the forward travel direction of the user at the first pose. The movement vector may include an angular displacement of the user from the first pose to the second pose. The movement vector may also include a horizontal translation relative to the vertical gravitational axis of the user from the first pose to the second pose.

The user may have a center of gravity and the vertical gravitational axis may intersect the center of gravity of the user along a direction of gravity. At least one actuator may include at least one of a tri-axial accelerometer, a tri-axial magnetometer, or a tri-axial gyroscope. The inertial measurement sensor may be disposed on the band. At least one actuator may include at least one of an electro-mechanical polymer, a piezo-electric actuator, a solenoid actuator, a pneumatic actuator, a hydraulic actuator, or a linear actuator.

The operations may also include, when the movement vector satisfies a threshold movement vector, causing a display of a stationary virtual object on an electronic display in communication with the controller. The operations may further include, when the movement vector satisfies a threshold movement vector, triggering an ancillary feedback response comprising an audible response, a visual response, or a vibratory response.

Yet another aspect of the disclosure provides a second method of operation for a wearable. The method includes receiving, at data processing hardware, an inertial measurement from an inertial measurement sensor disposed on a user, determining, by the data processing hardware, a movement vector defining the movement of the user from the first pose to the second pose based on the inertial measurement, and determining, by the data processing hardware, whether the movement vector satisfies a threshold movement vector. The user defines a vertical gravitational axis and a forward travel direction. The user has a pose defined by a sway angle of the user relative to the vertical gravitational axis and a sway direction of the user relative to the forward travel direction. The inertial measurement may be indicative of a movement of the user from a first pose to a second pose away from the first pose. The movement vector may be relative to the first pose. When the movement vector satisfies a threshold movement vector, the method includes instructing, by the data processing hardware, display of a stationary virtual object on an electronic display.

This aspect may include one or more of the following optional features. In some implementations, determining whether the movement vector satisfies a threshold movement vector includes determining whether the movement vector extends beyond a movement envelope defined by a collection of envelope movement vectors relative to the vertical gravitational axis and the forward travel direction of the user at the first pose. The movement vector may include an angular displacement of the user from the first pose to the second pose. The movement vector may include a horizontal translation relative to the vertical gravitational axis of the user from the first pose to the second pose. The user may have a center of gravity and the vertical gravitational axis may intersect the center of gravity of the user along a direction of gravity. At least one inertial measurement sensor may include at least one of a tri-axial accelerometer, a tri-axial magnetometer, or a tri-axial gyroscope. At least one actuator and the inertial measurement sensor may be disposed on a band wearable by the user.

Instructing the display of the stationary virtual object may include receiving a feed of an environment about the user, augmenting the feed by adding the stationary virtual object to the feed, and displaying the augmenting feed on the electronic display. The stationary virtual object may indicate the vertical gravitational axis. The electronic display may include a head mounted display. The feedback response may include at least one of a force at least partially opposite to and proportional to the movement vector, an audible signal, an emitted light, or a vibration.

The details of one or more implementations of the disclosure are set forth in the accompanying drawings and the description below. Other aspects, features, and advantages will be apparent from the description and drawings, and from the claims.

DESCRIPTION OF DRAWINGS

FIG. 2C is a front perspective view of an example actuator for a wearable.

FIG. 2D is a side view of the actuator shown in FIG. 2C.

Like reference symbols in the various drawings indicate like elements.

DETAILED DESCRIPTION

The present disclosure provides systems and methods for sensing movement of a user and providing feedback to the user based on an identification of the movement of the user. A wearable donned by the user senses the movement of the user and when the movement is outside a typical range of movements (e.g., postural body sway representative of normal balance) or is indicative of an imminent fall, the wearable provides the user a feedback response, which the user can use to correct his/her movements and/or avoid the fall. In some examples, during normal activities, the wearable continually monitors head movement of the user and when the head movement exceeds a threshold movement, imparts motion-proportionate forces to the head of the user to alert the user of the irregular head movements. The imparted forces may be proportional to the head movement and in a direction opposite of the head movement (e.g., as to mimic pushing the user back to a safe position). The forces generated by the wearable may be perceived by the user as reactive loads to help stabilize the head of the user, thereby improving the user's ability to sense and correct for imbalance, and ultimately train the user to improve and maintain balance without the need for continually wearing the wearable.

Figure 1A:
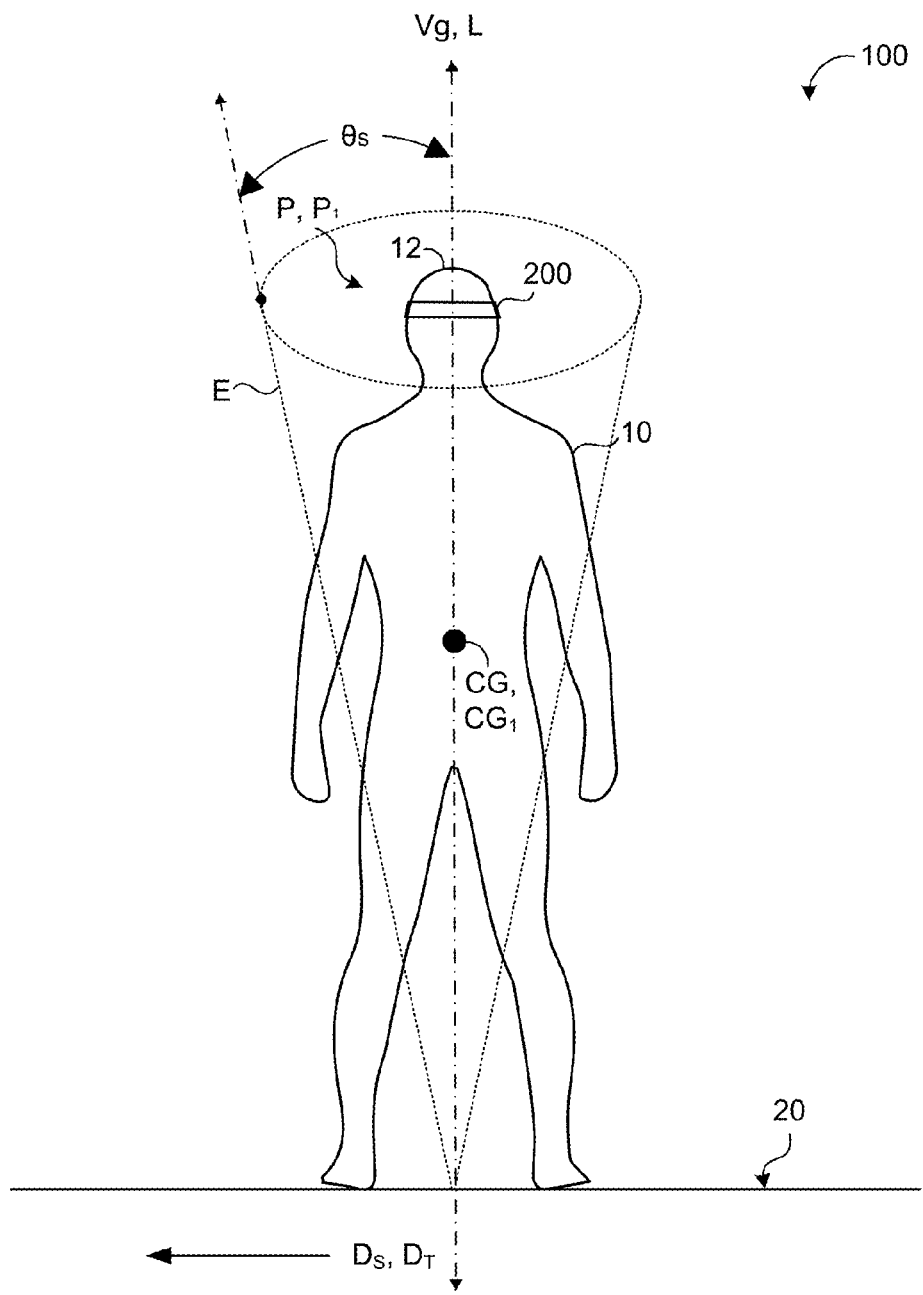
FIG. 1A is a schematic view of an example feedback environment for a user.
Figure 1B:
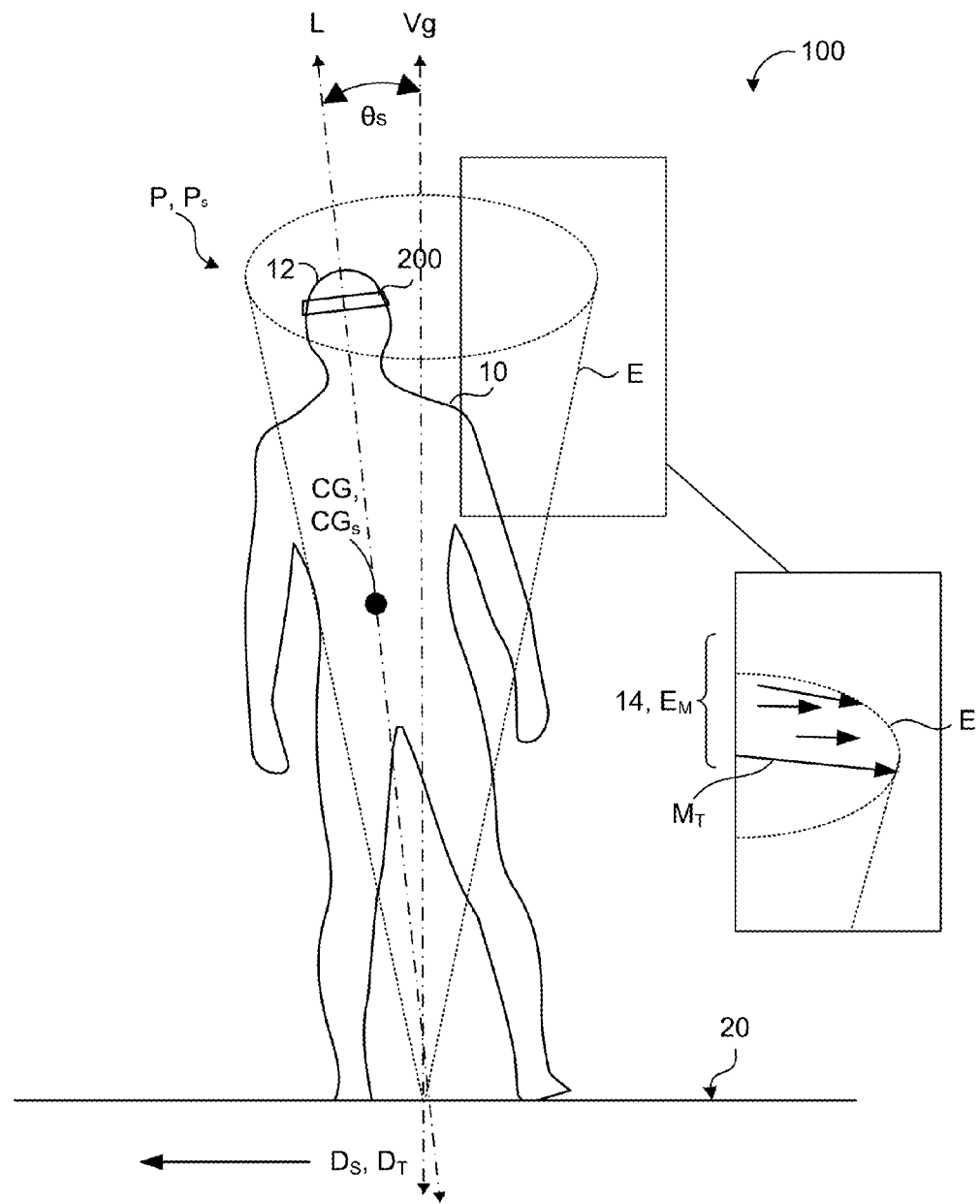
FIG. 1B is a schematic view of the example feedback environment of FIG. 1 including movement of the user.
Figure 1C:
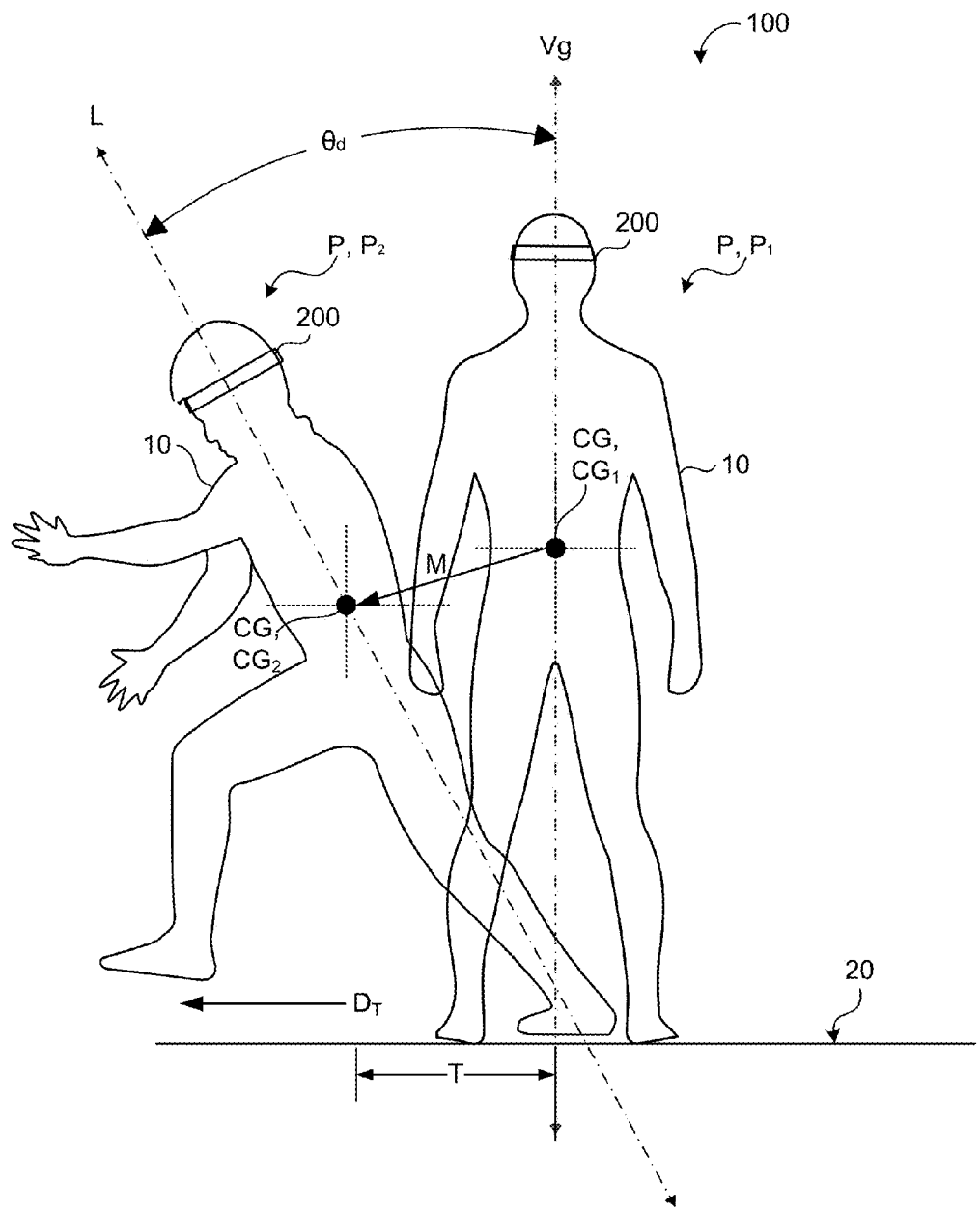
FIG. 1C is a schematic view of the example feedback environment of FIG. 1 including movement of the user.

FIGS. 1A-C illustrate a user 10 in an example feedback environment 100 wearing a wearable 200. Referring to FIG. 1A, the user 10 has a longitudinal axis L and vertical gravitational axis $V_g$, which is perpendicular to ground 20 along a direction of gravity. The longitudinal axis L of the user 10 may be coincident with the vertical gravitational axis $V_g$ when the user 10 is standing straight up and vertical. The user 10 has a center of gravity CG, which is a point where the user 10 has a zero sum distribution of mass. The longitudinal axis L of the user 10 intersects the center of gravity CG of the user 10. Moreover, the user 10 has a pose P defined by a sway angle $\theta_s$ of the user 10 relative to the vertical gravitational axis $V_g$ and a sway direction Ds of the user 10 relative to a forward travel direction $D_T$ of the user 10. The pose P of the user 10 defines a particular attitude or stance assumed by the user 10. The attitude of the user 10 can be defined by an orientation or an angular position of an object in space. For example, the pose P of the user 10 can be defined as the sway angle $\theta_s$ of the user 10 between the longitudinal axis L and the vertical gravitational axis $V_g$ and the sway direction Ds (e.g., an angle) of the user 10 relative to the forward travel direction $D_T$.

The wearable 200 defines a vertical axis $V_w$. In some implementations, when the user 10 dons the wearable 200, the user 10 arranges the wearable 200 such that the vertical axis $V_w$ of the wearable 200 is coincident or substantially coincident with the longitudinal axis L of the user 10. In additional implementations, the wearable 200 includes or defines a locating feature, such as a poka yoke, that causes the wearable 200 to become seated on the user 10 in an orientation such that the vertical axis $V_w$ of the wearable 200 is coincident or substantially coincident with the longitudinal axis L of the user 10. For example, a hat including the wearable 200 causes the user 10 to don the wearable in substantially consistent manner and in a substantially consistent position and/or orientation with respect to the center of gravity CG and the longitudinal axis L of the user 10.

In the example shown in FIG. 1B, the user 10 is positioned at a sway pose P, $P_s$ with a sway center of gravity CG, $CG_s$. The user 10 has an associated movement envelope E that defines a volume of space the user 10 can move or sway within without losing balance and/or falling. The movement envelope E is defined by a collection 14 of envelope movement vectors $E_M$ relative to the vertical gravitational axis $V_g$ and the forward travel direction $D_T$ of the user 10. A threshold movement vector $M_T$ may be one of the envelope movement vectors $E_M$ defining the movement envelope E or inferred based on the movement envelope E to be coincident a movement vector M. In some implementations such as balance training, the threshold movement vector $M_T$ is representative of normal postural sway for the user 10. When the threshold movement vector $M_T$ is representative of normal postural sway for the user 10, balance training would allow the user 10 to correct balance before losing balance and/or falling. In some examples, normal postural sway, depending on age, has the sway angle $\theta_s$ of the user 10 of about one to two degrees between the longitudinal axis L and the vertical gravitational axis $V_g$. The threshold movement vector $M_T$ would represent the sway angle $\theta_s$ of the user 10 of about one to two degrees between the longitudinal axis L and the vertical gravitational axis $V_g$.

In the example shown in FIG. 1C, the user 10 moves from a first pose P, $P_1$ to a second pose P, $P_2$, causing a center of gravity CG, $CG_1$ of the first pose $P_1$ to translate via the motion to a center of gravity CG, $CG_2$ of the second pose $P_2$. The movement of the user 10 may be quantified as the movement vector M defined by an angular displacement $\theta_d$ and a horizontal translation T relative to the vertical gravitational axis $V_g$ of the user 10 from the first pose $P_1$ to the second pose $P_2$. The movement envelope E is pinned to the user 10 and moves with the user 10. For example, the movement envelope E of the user 10 at the first pose $P_1$ has a different position and orientation (e.g., a different attitude) than the movement envelope E of the user 10 at the second pose $P_2$.

As the user 10 moves from the first pose $P_1$ to the second pose $P_2$, the wearable 200 senses the movement of the user 10 and determines a movement vector M quantifying the movement. The wearable 200 determines whether the movement vector M satisfies the threshold movement vector $M_T$. In some examples, the wearable 200 determines whether the movement vector M extends beyond the movement envelope E (the volume of movement space wherein the user 10 maintains normal postural sway). When the movement vector M satisfies the threshold movement vector $M_T$ (e.g., by extending beyond the movement envelope E), the wearable 200 delivers a feedback response to the user 10, prompting the user 10 to correct a potentially hazardous movement or resulting pose P that may cause a loss of balance or a fall. The feedback response may have one or more characteristics (e.g., a direction, a magnitude, a duration, a modulation, etc.) proportional or equal to the movement vector M and/or a difference between the movement vector M and the threshold movement vector $M_T$. The feedback response may be haptic (via an applied force), audible, visual, etc.

Figure 2A:
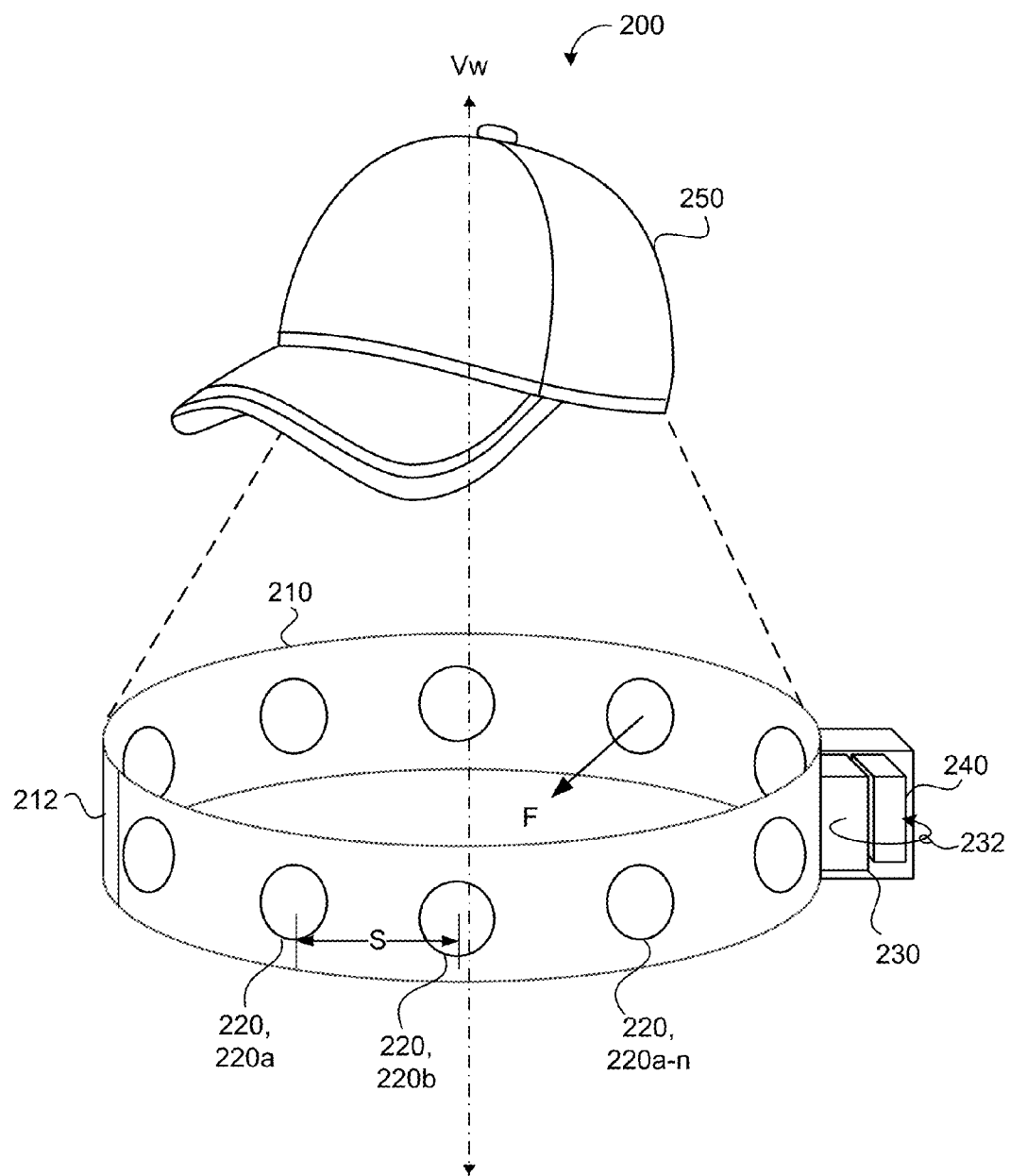
FIG. 2A is a perspective view of an example wearable.

FIG. 2A illustrates an example wearable 200 that delivers the feedback response to the user 10. The wearable 200 includes a band 210, actuators 220 disposed on the band 210, an inertial measurement sensor 230, and a controller in communication with the actuators 220 and the inertial measurement sensor 230. In the example shown, a head-worn garment 250 (e.g., a hat) donnable by the user 10 includes the wearable 200. In other examples, the wearable 200 is implemented as a band configuration worn around the user 10, such as a chest strap, a shirt, a vest, a waist-worn belt, a neck collar, an ankle band, a wrist band, a finger band, a helmet, or other user accessory.

The band 210 is positioned on the user 10 such that the user 10 perceives (e.g., feels, hears, or sees) the feedback response from the wearable 200. The user 10 may perceive the feedback response anywhere on the user 10 or anywhere at or near the wearable 200. In some examples, the band 210 perimetrically surrounds a portion of the user 10 to sense directions of movement and/or to deliver the feedback response. For example, FIG. 2A illustrates the band 210 of the wearable 200 positioned on the head 12 of the user 10 via the head-worn garment 250. When circumferentially around the head 12 of the user 10, the band 210 of the wearable 200 may sense forward, backward, or lateral movement. Since a user 10 may vary in size or in shape, the band 210 is configured to adjust for the user 10 to enable the band 210 to be sized in close approximation to a surface of the user 10. In some implementations, the band 210 accommodates for different users by a band adjustor 212. The band adjustor 212 may be in-line with the band 210 or have an overlapping configuration. Example configurations for the band adjustor 212 are pinlock adjustors, ratchet adjustors, hook and loop fastener adjustors, or linkage adjustors. Other configurations are possible as well, such as an elastic band.

The actuators 220 are circumferentially spaced along the band 210 with a spacing S between each actuator 220. For example, a first actuator 220, 220a is spaced by a spacing S apart from a second actuator 220, 220b. Moreover, the actuators 220 may be evenly or unevenly spaced. The actuators 220 are configured to apply a force F (e.g., a diametric force) to a user 10 donning the band 210. The diametric force F is in a direction opposite and proportional to the movement of the user 10 from the first pose $P_1$ to the second pose $P_2$. The number of actuators 220 circumferentially spaced along the band 210 depends on a level of precision for the feedback response and may distribute counter forces on the side opposite the diametric force F. For example, the wearable 200 with two actuators 220a, 220b may impart a combined force between directions nearest to one of the two actuators 220a, 220b in order to generate the diametric force F. Whereas, a wearable 200 with eight actuators 220, 220a-i may apply the diametric force F to an actuator 220 more closely relating to the direction of the movement between the first pose $P_1$ and the second pose $P_2$. In some examples, at least one actuator 220 applies the diametric force F while the opposite side of the band 210 applies a broadly distributed reaction force. In the example shown in FIG. 2A, ten actuators 220, 220a-j circumscribe the head 12 of the user 10. Other arrangements are possible as well with any number of actuators 220 (e.g., one continuous actuator 220 about the head 12 of the user 10). The actuators 220 may be electromechanical actuators, such as electromechanical polymers, piezo-electric actuators, solenoid actuators, pneumatic actuators, hydraulic actuators, or linear actuators.

In some examples, at least one actuator 220 is configured to output a feedback response, such as a sound, a vibration, or light. The feedback response may be in addition to the diametric force F or independent from the diametric force F. As examples, the at least one actuator 220 may include a vibration motor, a linear resonant actuator, a light emitting diode, an audio signaling device, such as a beeper or a buzzer, or other electrical component capable of providing the feedback response.

The inertial measurement sensor 230 is configured to measure an inertial measurement 232 indicative of a movement of the user 10 from a first pose $P_1$ to a second pose $P_2$ away from the first pose $P_1$. The inertial measurement 232 may be the horizontal translation T of the center of gravity CG of the user 10 from the first pose $P_1$ to the second pose $P_2$ or an angular change of the wearable 200 as the wearable 200 moves with the user 10 from the first pose $P_1$ to the second pose $P_2$. The inertial measurement sensor 230 may detect and may measure an acceleration, a tilt, a shock, a vibration, or a rotation of the user 10, as the inertial measurement 232, using the first pose $P_1$ as an inertial reference frame. In some examples, the inertial measurement sensor 230 produces three dimensional measurements of a specific force and an angular rate. The inertial measurement sensor 230 may include at least one of a tri-axial accelerometer, a tri-axial magnetometer, or a tri-axial gyroscope. The inertial measurement sensor 230 may also include a microprocessor.

A controller 240 is configured to process data relating to the user 10 or the wearable 200. The controller 240 receives an inertial measurement 232 from the inertial measurement sensor 230 (e.g., via a wired or wireless connection) disposed on the user 10. The controller 240 determines the movement vector M defining the movement of the user 10 from the first pose $P_1$ to the second pose $P_2$ based on the inertial measurement 232, the movement vector M being relative to the first pose $P_1$. The controller 240 decides whether the movement vector M satisfies the threshold movement vector $M_T$. When the movement vector M satisfies the threshold movement vector $M_T$, the controller 240 instructs at least one actuator 220 to apply the diametric force F, at least partially opposite to and proportional to the movement vector M, on the user 10.

In some implementations, the threshold movement vector $M_T$ is set to zero such that the controller 240 instructs at least one actuator 220 to apply the feedback response on the user 10 when the controller 240 determines any movement vector M has occurred by the user 10. Alternatively or additionally, the threshold movement vector $M_T$ is variable based on activity such that the controller 240 may apply different feedback responses depending on the movement vector M. In some examples, the controller 240 applies one type of feedback response (e.g., sound, vibration, light, or force) or pattern of feedback responses when the movement vector M satisfies the threshold movement vector $M_T$ and another type of feedback response (e.g., sound, vibration, light, or force) or pattern of feedback responses when the movement vector M extends beyond the movement envelope E.

In some examples, the movement vector M satisfies the threshold movement vector $M_T$ when the movement vector M extends beyond the movement envelope E or the volume of movement space wherein the user 10 maintains balance. The user 10 or a third party may train or define the movement envelope E or pre-program the movement envelope E in the controller 240. For example, the controller 240 may execute a training routine that stores training movement vectors M indicative of the movement envelope E (e.g., in non-transitory memory of controller 240). Additionally or alternatively, the controller 240 may learn the movement envelop E of the user 10 via the stored movement vectors M, a prescribed movement routine for the user 10 to carryout, or a learned pattern of movements of the user 10 over time. In some examples, the controller 240 identifies patterns in the movement vectors M determined by changes in the inertial measurements 232 between poses (e.g., between the first pose $P_1$ to the second pose $P_2$). The controller 240 may normalize the movement vectors M to define movements of the user 10 wherein the user 10 maintains balance. The controller 240 may define the threshold movement vector $M_T$ as a movement vector M that represents a boundary of the movement envelope E. In some examples, the controller 240 identifies that the movement vector M satisfies the threshold movement vector $M_T$ when the movement vector M is an anomaly of the collection 14 of envelope movement vectors $E_M$.

In some implementations, the user 10 has a third party or a programming device pre-program the movement envelope E in the controller 240. In such implementations, a modeling or a computation program determines the collection 14 of envelope movement vectors $E_M$ and/or the threshold movement vector $M_T$ based on a set of characteristics of the user 10. The set of characteristics may include age, gender, height, or other physiological characteristics. A smartphone, tablet, computer, a remote based-cloud application or other application system may execute the modeling or the computation program.

In additional examples, the controller 240 instructs at least one actuator 220 to apply the diametric force F depending on a shape of the band 210 or how many actuators 220 are included on the shape of the band 210. The number of actuators 220 circumferentially spaced along the band 210 depends on a level of precision for the feedback response. In some configurations, the controller 240 interpolates directions of movement of the user 10 to apply the diametric force F at least partially opposite to and proportional to the movement vector M. For example, the wearable 200 with two actuators 220a, 220b may impart a combined force between directions nearest to one of the two actuators 220a, 220b in order to generate the diametric force F. Whereas, a wearable 200 with eight actuators 220, 220a-i may apply the diametric force F via one actuator 220 or a combination of actuators 220, 220a-i closely relating to the direction of the movement between the first pose $P_1$ and the second pose $P_2$. In some examples, the incremental spacing S between the actuators 220, 220a-n is close enough that one given actuator 220 aligns with a proposed direction of the diametric force F.

In some implementations, the controller 240 instructs at least one actuator 220 to continuously apply the diametric force F proportional to the movement vector M. The diametric force may be linear or non-linear. As an example, the diametric force F may be like that of a spring force, F=Kx, where the diametric force F, like the displacement x of the spring force, is proportional to the movement vector M such that as the movement vector M decreases or increases in magnitude the diametric force F applied by at least one actuator 220 will decrease or increase respectively.

Additionally or alternatively, the controller 240 may be configured to instruct at least one actuator 220 to apply the diametric force F by displacement control or by force-control. In examples of displacement control, the controller 240 outputs a current capable of changing a position of at least one actuator 220. Whereas, in examples of force control, the controller 240 communicates with at least one load transducer paired with at least one actuator 220. With the load transducer, the controller 240 may receive an electrical signal from the load transducer proportional to a force measured by the load transducer at a position of the load transducer. The controller 240 may interpret the electrical signal from the load transducer to instruct the actuator 220 to apply the diametric force F related to the force measure by the load transducer.

Figure 2B:
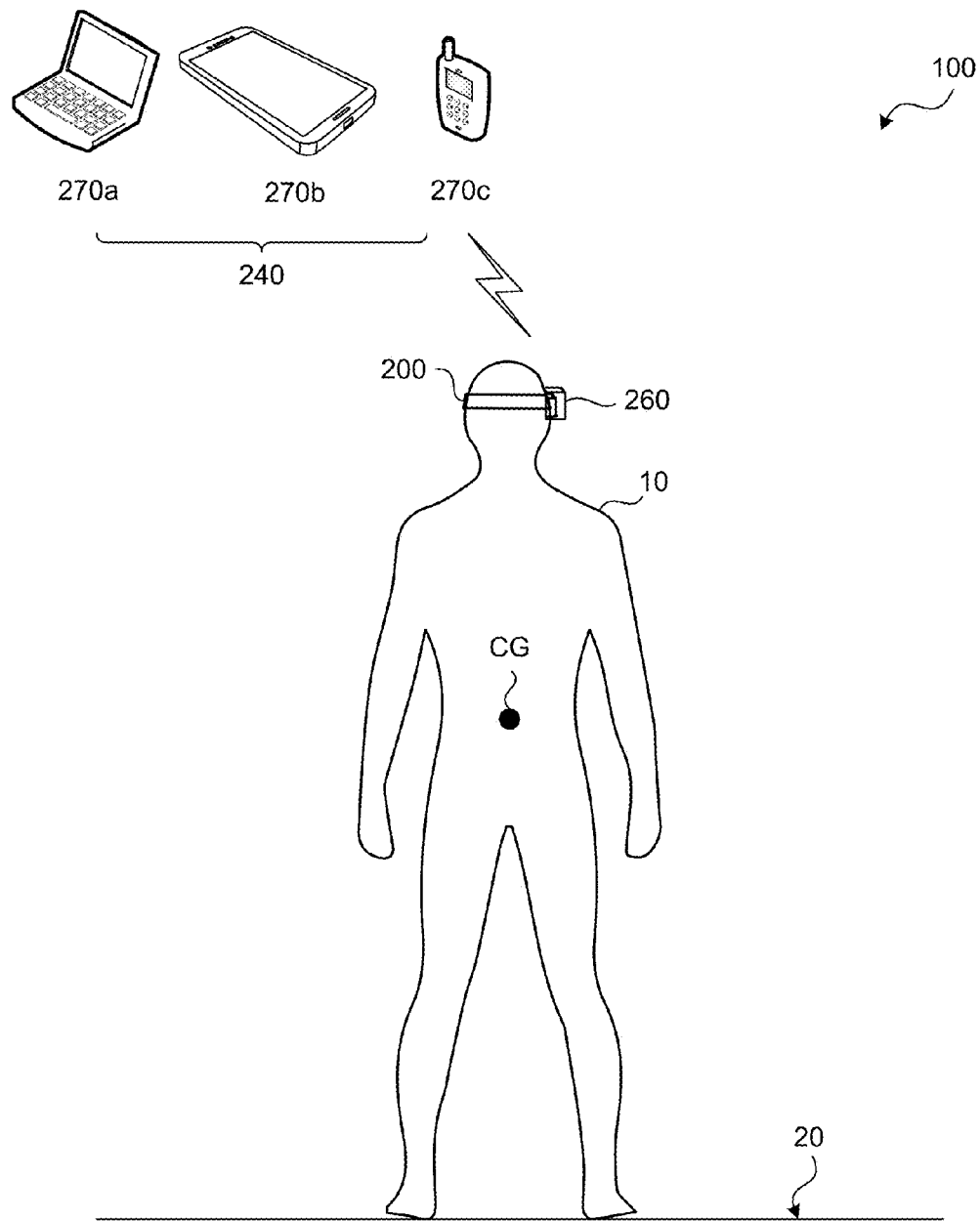
FIG. 2B is a schematic view of an example wearable having a controller separate from a band of the wearable.

In the example shown in FIG. 2B, the controller 240 is disposed on the band 210 of the wearable 200. When disposed on the band 210 of the wearable 200, the controller has wiring circuitry (e.g., a wiring harness) capable of communicating with the inertial measurement sensors 230 and at least one actuator 220. In other examples, such as in FIG. 2B, the controller 240 is separate from the band 210 of the wearable 200. In such examples, the controller 240 is configured for wired communication (via wired tether) or wireless communication (e.g., via Bluetooth compatible circuitry) with the inertial measurement sensors 230 and/or at least one actuator 220. For example, the controller 240 may be a mobile device 270 (e.g., a laptop 270a, a tablet 270b, mobile phone 270c, etc.) having a wireless connection (e.g., Bluetooth) to a wireless connector 260 disposed on the band 210. The wireless connector 260 relays communications between the controller 240 and the at least one actuator 220. Additionally, the mobile device 270 may include the inertial measurement sensors 230. Otherwise, the wireless connector 260 relays communications between the controller 240 and the inertial measurement sensors 230 on the band 210 as well. In some implementations, the controller 240 is removably attached to the band 210 of the wearable 200 such that the user 10 may attach the controller 240 to another portion of the user 10. When the controller 240 is removably attached, the controller 240 may include physical wiring tethering the controller 240 to the band 210 of the wearable 200 or a wireless configuration.

Referring to FIGS. 2C and 2D, in some implementations, the actuator 220 generates a motion-proportionate displacement for the user 10 to perceive varying magnitudes of the diametric force F. In the example shown, the actuator 220 is an electromechanical polymer (EMP), also known as an electro-active polymer (EAP), artificial muscle, or a di-electric elastomeric actuator (DEA). Generally, electromechanical polymers are polymers that deform when stimulated by an electric field. In the example shown, the actuator 220 defines a long axis $A_L$, a short axis $A_S$ perpendicular to the long Axis $A_S$, and a force axis $A_F$ orthogonal to the long axis $A_L$ and the short axis $A_S$. The actuator 220 may have a configuration to produce a first displacement $\Delta y$ by bending along the long axis $A_L$ to create an arch 222 at its center or in a cantilever beam configuration to produce a second displacement $\Delta x$ at the end of the long axis $A_L$. As shown, the displacement, $\Delta x$ or $\Delta y$, may impart the diametric force F by the actuator 220 along the force axis $A_F$.

Alternatively, the actuator 220 may be other types of electro-mechanical or mechanical actuators, such as solenoid actuators, pneumatic actuators, hydraulic actuators, linear actuators, or inflatable bladders. For these types of actuators, an electrical signal from the controller 240 actuates an electro-mechanical or mechanical structure of the actuator 220 to impart the diametric force F on the user 10. For example, in a simple solenoid actuator, the electrical signal from the controller 240 induces a magnetic field to produce a mechanical response by a mechanical structure, such as a plunger or rod. In such example, the electrical signal strength determines an amount of the mechanical response by the mechanical structure of the simple solenoid actuator.

The vibrotactile, gyroscope-based force actuators, and other prior approaches have limitations that make them impractical and/or unsuitable for mainstream adoption. For example, vibrotactile actuators do not apply reactive and motion-proportionate forces to the user. Gyroscope-based actuators also suffer from various shortcomings. For example, gyroscope-based actuators can only impart moments (rotational force) to the user and thus do not create adequate sensations of reactive force that are useful for signaling small or even moderate levels of imbalanced motion. Gyroscope-based actuators (and their required power sources) are generally not available in a size and configuration that can be comfortably worn by elderly or frail users for extended durations, such as during normal activities of daily living, further limiting their practicality and applicability as a wearable solution. On the other hand, the actuators 220 of the wearable 200 (e.g., electromechanical actuators) can be light weight, flexible, low power consumption, and/or manufactured in large volumes to achieve low unit cost. Gyroscope-based actuators may also counterintuitively accentuate the imbalance of the user rather than compensate for imbalance.

Figure 2E:
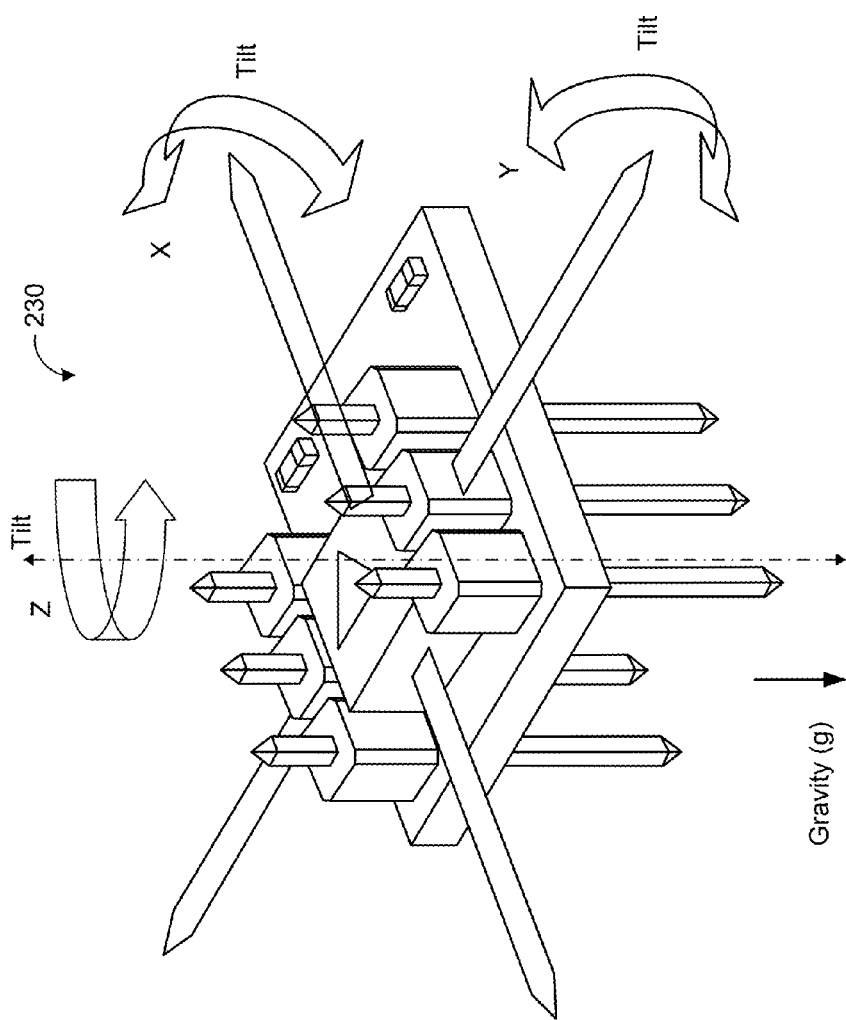
FIG. 2E is a perspective view of an example inertial measurement sensor.

FIG. 2E illustrates an example inertial measurement sensor 230. The inertial measurement sensor 230 is a circuit configured to detect and to measure the acceleration, the tilt, the shock, the vibration, or the rotation of the user 10. To detect and to measure, the inertial measurement sensor 230 may include at least one of a tri-axial accelerometer, a tri-axial magnetometer, or a tri-axial gyroscope. The tri-axial accelerometer includes circuitry to sense the movement of a user 10 between poses (e.g., between the first pose and the second pose) along a straight line or an axis, such as a position and an orientation of the inertial measurement sensor 230. In some examples, the accelerometer may use a mass-spring system or a vibration system configured to determine an acceleration corresponding to a displacement of a mass in the mass-spring system or a stress related to a vibration in the vibration system. The inertial measurement sensor 230 may also include a gyroscope, such as the tri-axial gyroscope, to measure a rate of rotation about a defined axis. The gyroscope is configured to sense rotation of the inertial measurement sensor 230 such that a sensed rotation is a portion of the inertial measurement 232 output to the controller 240. The controller 240 receives the inertial measurement 232 of the inertial measurement sensor 230 and determines movements of the user 10 relative to the wearable 200. Thus, the gyroscope senses rotations of the user 10 as the user 10 moves with the wearable 200. The inertial measurement sensor 230 may include more than one of the tri-axial accelerometer, the tri-axial magnetometer, or the tri-axial gyroscope to increase accuracy of the inertial measurement sensor 230. The inertial measurement sensor 230 may be positioned on the wearable 200, the controller 240, or other portions of the user 10.

Although the wearable 200 provides a solution for falls among the elderly or older adults, the wearable 200 may be useful in many other ways for improving body control and providing navigational guidance. For example, the wearable 200 could be useful in activities demanding controlled movement of a portion of the user 10. In some instances, the wearable 200 controls movements within particular activities, such as: stabilizing the head of a baseball player or a golfer during a swing; directing a basketball shot form of a basketball player; stabilizing the aim of a sharp-shooter, stabilizing surgical hand motion; or other related motion control activities. The wearable 200 may also guide navigational activities, such as walking, running cycling, driving, or flying. Navigational guidance by the wearable 200 may be advantageous for the user 10 with hearing or sight impairment or for the user in environments with insufficient lighting, high background noise, or generally compromised means of communication.

In some implementations, the wearable 200 assists navigation for the user 10. In such implementations, at least one actuator 220 provides the feedback response in a desired direction of travel to direct the user 10 to move from the first pose P1 to the second pose P2 in the desired direction of travel. Additionally or alternatively, the controller 240 may communicate to apply a pattern of feedback responses as guidance instructions, such as stop, turn right, or turn left, as some examples. The feedback response may be a force, a vibration, a sound, or other perceivable response to the user 10. The controller 240 may include or communicate with global positioning or mapping software to further assist in navigation of the user 10.

The controller 240 of the wearable 200 may quantify the movement vector M in different ways. In some examples, the controller 240 quantifies the movement vector M by using an angular displacement $\theta_d$, $\theta_w$ of the wearable 200 and a horizontal translation T, $T_w$ of the wearable 200 relative to the wearable axis $V_w$ of the wearable 200 at the first pose $P_1$. Additionally or alternatively, the controller 240 quantifies the movement vector M by using an angular displacement $\theta_d$, $\theta_u$ of the center of gravity CG of the user 10 and a horizontal translation T, $T_u$ of the user 10 relative to the vertical gravitational axis $V_g$ of the user 10 at the first pose $P_1$. In some examples, the controller 240 quantifies the movement vector M by using the angular displacement $\theta_d$, $\theta_s$ of the inertial measurement sensor 230 and a horizontal translation T, $T_s$ of the inertial measurement sensor 230.

Figure 3:
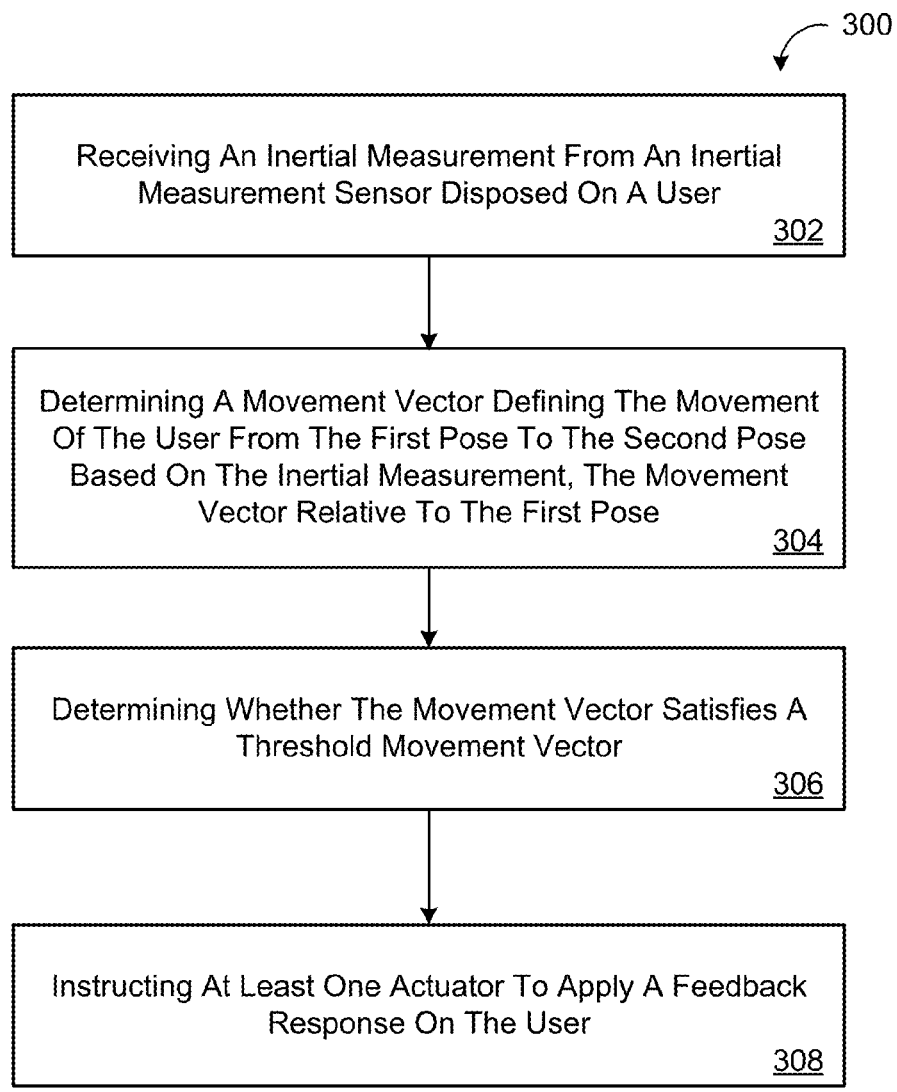
FIG. 3 is a flowchart of an example arrangement of operations of a method for providing feedback to a user based on an identification of movement of the user.

FIG. 3 provides an example arrangement of a method 300 of operation for a wearable 200. At block 302, the method 300 includes receiving, at data processing hardware (e.g., the controller 240), an inertial measurement 232 from an inertial measurement sensor 230 disposed on a user 10. The user 10 defines a vertical gravitational axis $V_g$ and a forward travel direction $D_T$. Moreover, the user 10 has a pose P defined by a sway angle $\theta_s$ of the user 10 relative to the vertical gravitational axis $V_g$ and a sway direction $D_S$ of the user 10 relative to the forward travel direction $D_T$. The inertial measurement 232 is indicative of a movement of the user 10 from a first pose $P_1$ to a second pose $P_2$ away from the first pose $P_1$. At block 304, the method 300 includes determining, by the data processing hardware, a movement vector M defining the movement of the user 10 from the first pose $P_1$ to the second pose $P_2$ based on the inertial measurement 232. The movement vector M is relative to the first pose $P_1$. At block 306, the method 300 includes determining, by the data processing hardware, whether the movement vector M satisfies a threshold movement vector $M_T$. At block 308, the method 300 includes instructing, by the data processing hardware, at least one actuator 220 to apply a feedback response on the user 10. The force F at least partially opposite to and proportional to the movement vector M when the movement vector M satisfies a threshold movement vector $M_T$.

In some implementations, determining whether the movement vector M satisfies a threshold movement vector $M_T$ includes determining whether the movement vector M extends beyond a movement envelope E defined by a collection 14 of envelope movement vectors $E_M$ relative to the vertical gravitational axis $V_g$ and the forward travel direction $D_T$ of the user 10 at the first pose $P_1$. The movement vector M may include an angular displacement $\theta_d$, $\theta_w$ of the user 10 from the first pose $P_1$ to the second pose $P_2$. The movement vector M may also include a horizontal translation T relative to the vertical gravitational axis $V_g$ of the user 10 from the first pose $P_1$ to the second pose $P_2$.

In some examples, the user 10 has a center of gravity CG and the vertical gravitational axis $V_g$ intersects the center of gravity CG of the user 10 along a direction of gravity. The at least one inertial measurement sensor 230 may include at least one of a tri-axial accelerometer, a tri-axial magnetometer, or a tri-axial gyroscope. The at least one actuator 220 and the inertial measurement sensor 230 may be disposed on a band 210 wearable by the user 10. The at least one actuator 220 may include at least one of an electro-mechanical polymer, a piezo-electric actuator, a solenoid actuator, a pneumatic actuator, a hydraulic actuator, or a linear actuator.

Instructing the at least one actuator 220 to apply the feedback response on the user 10 may include instructing a display of a stationary virtual object on an electronic display in communication with the data processing hardware. The feedback response may include at least one of a force at least partially opposite to and proportional to the movement vector M, an audible signal, an emitted light, or a vibration.

Figure 4A:
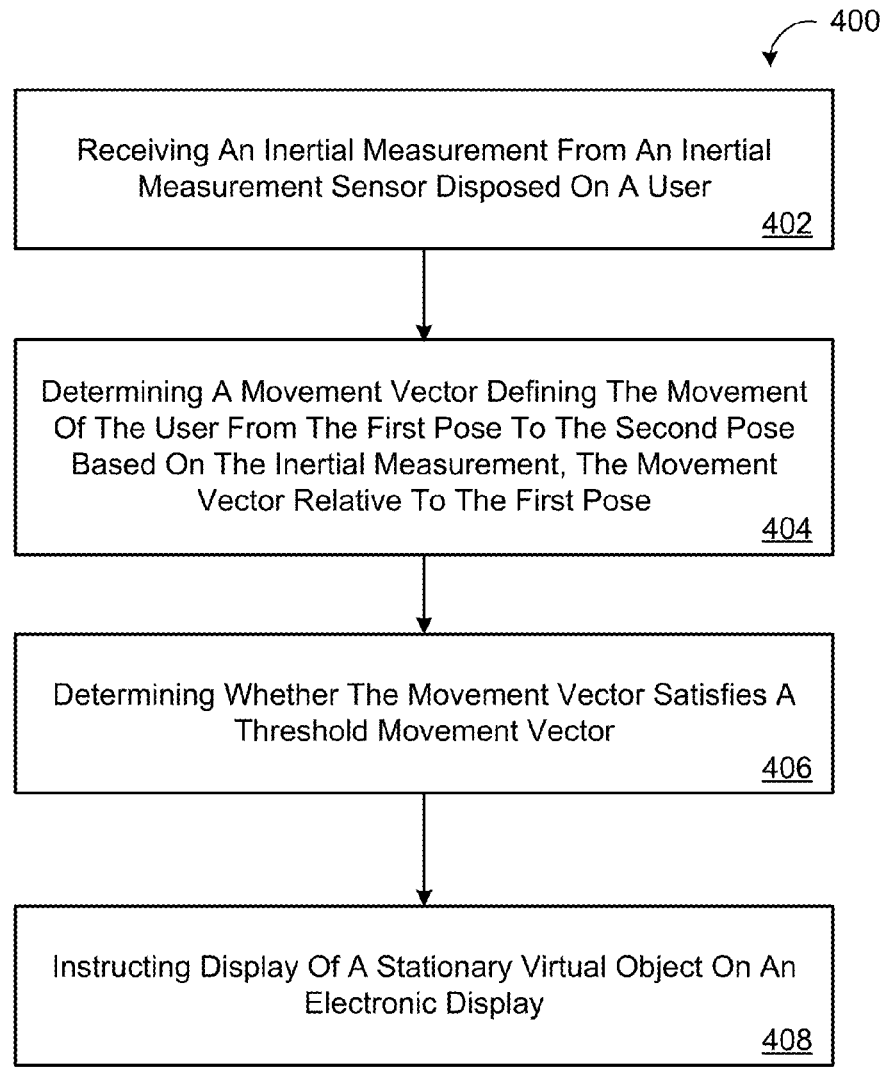
FIG. 4A is a flowchart of an example arrangement of operations of a method for providing feedback to a user based on an identification of movement of the user.
Figure 4B:
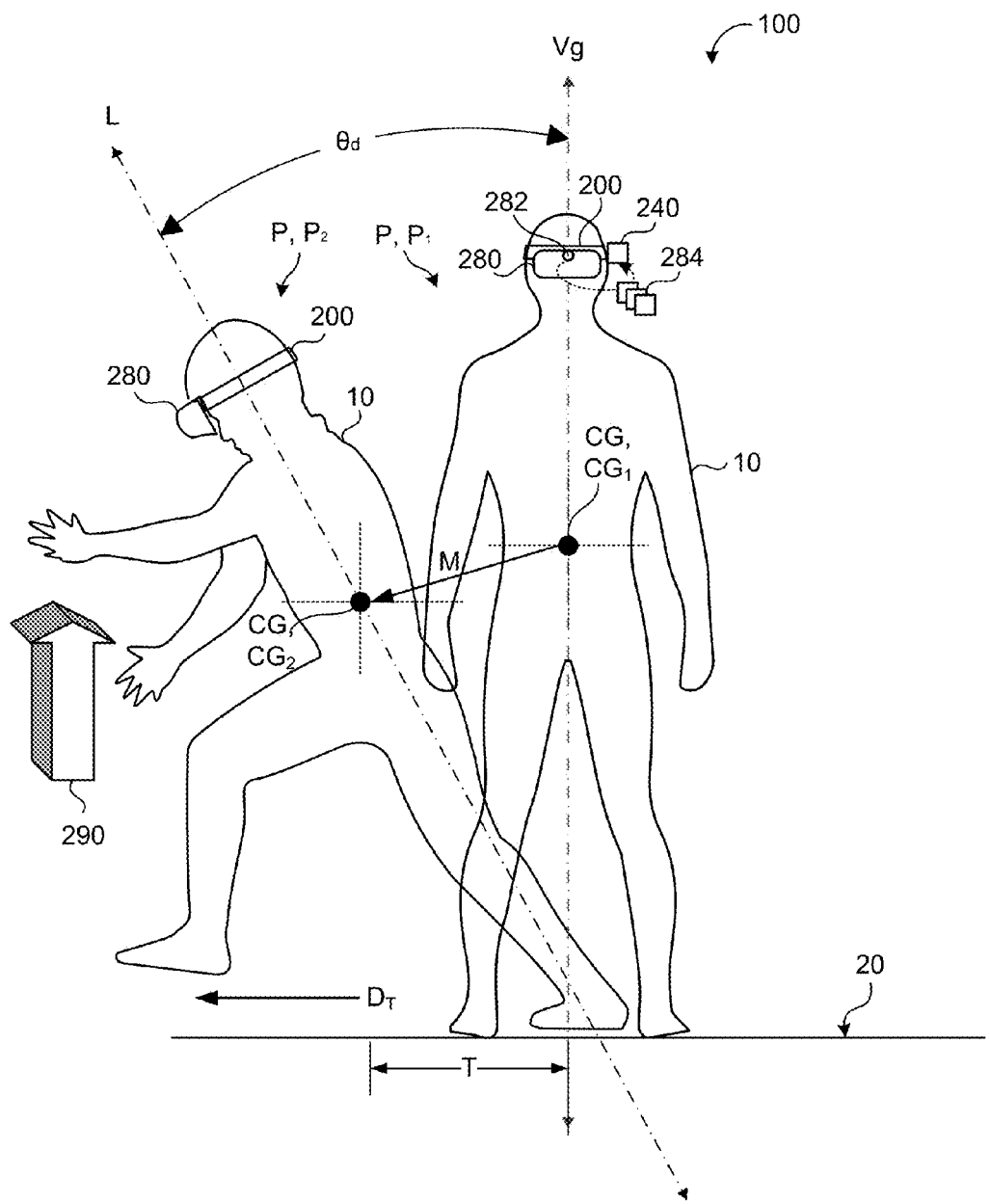
FIG. 4B is a schematic view of the example feedback environment including movement of the user.

FIG. 4A provides an example arrangement of a method 400 of operation for a wearable 200. FIG. 4B is a schematic view of the example feedback environment including movement of the user 10 donning the wearable 200. At block 402, the method 400 includes receiving, at data processing hardware (e.g. the controller 240), an inertial measurement 232 from an inertial measurement sensor 230 disposed on a user 10. At block 404, the method 400 includes determining, by the data processing hardware, a movement vector M defining the movement of the user 10 from the first pose $P_1$ to the second pose $P_2$ based on the inertial measurement 232. At block 406, the method 400 includes determining, by the data processing hardware, whether the movement vector M satisfies a threshold movement vector $M_T$. The user 10 defines a vertical gravitational axis $V_g$ and a forward travel direction $D_T$. The user 10 has a pose P defined by a sway angle $\theta_s$ of the user 10 relative to the vertical gravitational axis $V_g$ and a sway direction $D_S$ of the user 10 relative to the forward travel direction $D_T$. The inertial measurement 232 may be indicative of a movement of the user 10 from a first pose $P_1$ to a second pose $P_2$ away from the first pose $P_1$. The movement vector M may be relative to the first pose $P_1$. When the movement vector M satisfies a threshold movement vector $M_T$, at block 408, the method 400 includes instructing, by the data processing hardware, display on an electronic display 280 a stationary virtual object 290. Alternatively or additionally, the threshold movement vector $M_T$ may be set to zero such that the method 400 instructs the electronic display 280 to display the stationary virtual object 290 during any movement of the user 10. The stationary virtual object 290 may move with the user 10. Moreover, the stationary virtual object 290 may be a virtual pole or sign appearing to be anchored into the ground directly in front of and in close proximity to the user 10 to enhance visual sensory feedback, which has been shown to be important for maintaining balance and postural stability. During gait, the wearable 200 may virtually display a continuous guide rail, fence, or corridor in close proximity to the user and along which the user could walk. The electronic display 280 may wirelessly communicate with the inertial measurement sensor 230 or the controller 240, or could alternatively incorporate similar inertial measurement and processing elements to function as a stand-alone device. For users 10 with severely impaired eyesight due to degenerative diseases, such as cataracts or macular degeneration, the aforementioned stationary virtual objects 290 may be replaced with a field of view that varies from bright white when perfectly balanced to pitch black when unbalanced (or other color variations), and in between having fine gradations of light, which are proportional to the sway angle $\theta_s$ of the user 10.

In some implementations, determining whether the movement vector M satisfies a threshold movement vector $M_T$ includes determining whether the movement vector M extends beyond a movement envelope E defined by a collection 14 of envelope movement vectors $E_M$ relative to the vertical gravitational axis $V_g$ and the forward travel direction $D_T$ of the user 10 at the first pose $P_1$. The movement vector M may include an angular displacement $\theta_d$, $\theta_w$ of the user 10 from the first pose $P_1$ to the second pose $P_2$. The movement vector M may include a horizontal translation T relative to the vertical gravitational axis $V_g$ of the user 10 from the first pose $P_1$ to the second pose $P_2$. The user 10 may have a center of gravity CG and the vertical gravitational axis $V_g$ may intersect the center of gravity CG of the user 10 along a direction of gravity. At least one inertial measurement sensor 230 may include at least one of a tri-axial accelerometer, a tri-axial magnetometer, or a tri-axial gyroscope. At least one actuator 220 and the inertial measurement sensor 230 may be disposed on a band 210 wearable by the user 10.

In some implementations, the wearable 200 is a head mounted display (HMD) that includes an electronic display 280 (e.g., screen or projector) and an imaging sensor 282 (e.g., camera) in communication with the controller 240. The imaging sensor 282 captures images or a feed 284 of an environment about the user 10. In some examples, the feed 284 may be a transparent feed of the environment about the user 10 or a video feed input by the user 10 or a third party. Instructing the display of the stationary virtual object 290 may include receiving the feed 284 of the environment about the user 10, augmenting the feed 284 by adding the stationary virtual object 290 to the feed 284, and displaying the augmenting feed 284 on the electronic display 280. The stationary virtual object 290 may indicate the vertical gravitational axis $V_g$. The feedback response may include at least one of a force at least partially opposite to and proportional to the movement vector M, an audible signal, an emitted light, or a vibration.

Figure 5:
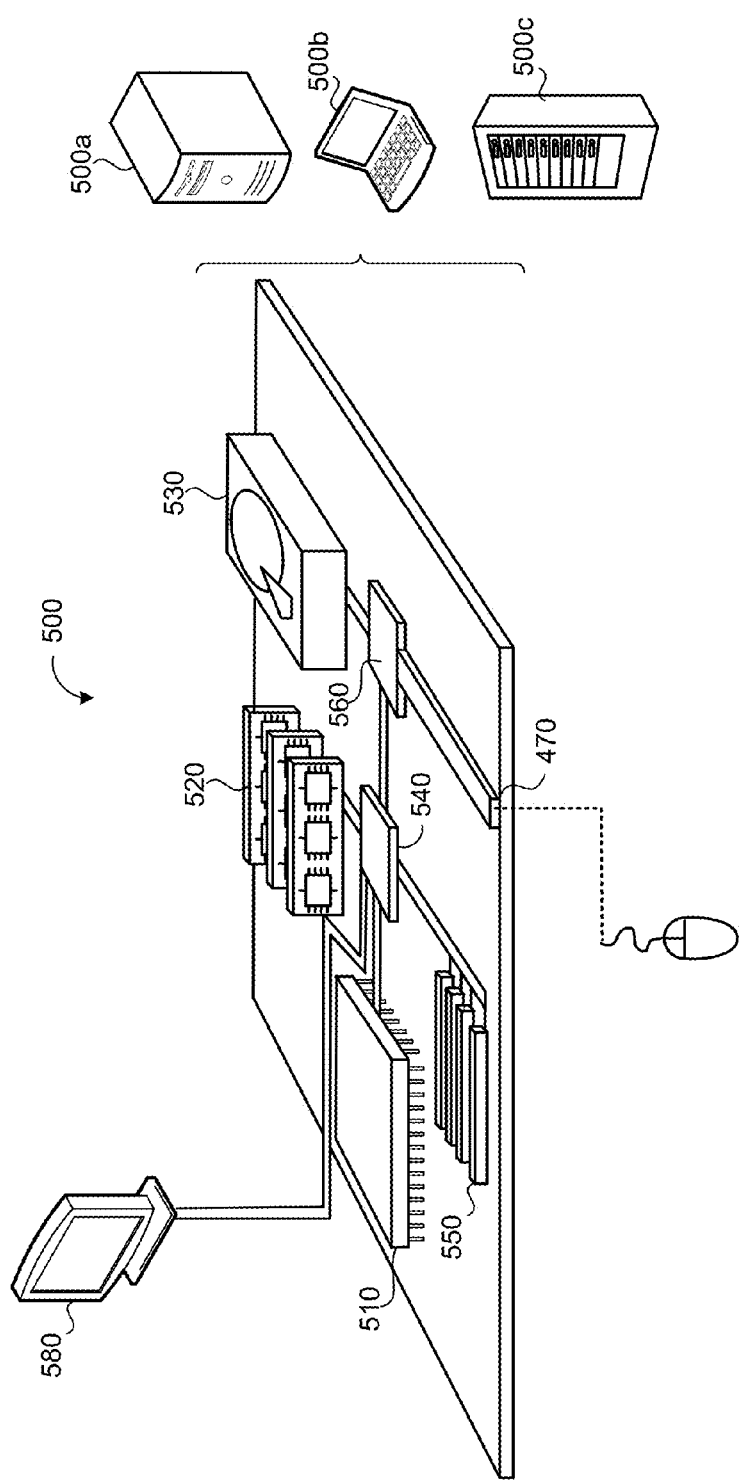
FIG. 5 is schematic view of an example computing device that may be used to implement the systems and methods of a feedback wearable.

FIG. 5 is schematic view of an example computing device 500 that may be used to implement the systems and methods described in this document. The computing device 500 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

The computing device 500 includes a processor 510, memory 520, a storage device 530, a high-speed interface/controller 540 connecting to the memory 520 and high-speed expansion ports 550, and a low speed interface/controller 560 connecting to low speed bus 570 and storage device 530. Each of the components 510, 520, 530, 540, 550, and 560, are interconnected using various busses, and may be mounted on a common motherboard or in other manners as appropriate. The processor 510 can process instructions for execution within the computing device 500, including instructions stored in the memory 520 or on the storage device 530 to display graphical information for a graphical user interface (GUI) on an external input/output device, such as display 580 coupled to high speed interface 540. In other implementations, multiple processors and/or multiple buses may be used, as appropriate, along with multiple memories and types of memory. Also, multiple computing devices 500 may be connected, with each device providing portions of the necessary operations (e.g., as a server bank, a group of blade servers, or a multi-processor system).

The memory 520 stores information non-transitorily within the computing device 500. The memory 520 may be a computer-readable medium, a volatile memory unit(s), or non-volatile memory unit(s). The non-transitory memory 520 may be physical devices used to store programs (e.g., sequences of instructions) or data (e.g., program state information) on a temporary or permanent basis for use by the computing device 500. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 530 is capable of providing mass storage for the computing device 500. In some implementations, the storage device 530 is a computer-readable medium. In various different implementations, the storage device 530 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 520, the storage device 530, or memory on processor 510.

The high speed controller 540 manages bandwidth-intensive operations for the computing device 500, while the low speed controller 560 manages lower bandwidth-intensive operations. Such allocation of duties is exemplary only. In some implementations, the high-speed controller 540 is coupled to the memory 520, the display 580 (e.g., through a graphics processor or accelerator), and to the high-speed expansion ports 550, which may accept various expansion cards (not shown). In some implementations, the low-speed controller 560 is coupled to the storage device 530 and low-speed expansion port 570. The low-speed expansion port 570, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 500a or multiple times in a group of such servers 500a, as a laptop computer 500b, or as part of a rack server system 500c.

Various implementations of the systems and techniques described herein can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The processes and logic flows described in this specification can be performed by one or more programmable processors executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A number of implementations have been described. Nevertheless, it will be understood that various modifications may be made without departing from the spirit and scope of the disclosure. Accordingly, other implementations are within the scope of the following claims.

What is claimed is:

1. A method comprising:
    receiving, at data processing hardware, an inertial measurement from an inertial measurement sensor disposed on a user, the inertial measurement sensor comprising a tri-axial accelerometer and a tri-axial gyroscope, the user defining a vertical gravitational axis and a forward travel direction, the user having a pose defined by a sway angle of the user relative to the vertical gravitational axis and a sway direction of the user relative to the forward travel direction, the inertial measurement indicative of a movement of the user from a first pose to a second pose away from the first pose;
    determining, by the data processing hardware, a movement vector defining the movement of the user from the first pose to the second pose based on the inertial measurement, the movement vector relative to the first pose;
    determining, by the data processing hardware, whether the movement vector satisfies a threshold movement vector; and
    when the movement vector satisfies a threshold movement vector, instructing, by the data processing hardware, at least one actuator to apply a feedback response on the user, the at least one actuator disposed on a band circumscribing a portion of the user, the feedback response comprising at least one force that is substantially opposite and proportional to the movement vector.

2. The method of claim 1, wherein determining whether the movement vector satisfies a threshold movement vector comprises determining whether the movement vector extends beyond a movement envelope defined by a collection of envelope movement vectors relative to the vertical gravitational axis and the forward travel direction of the user at the first pose.

3. The method of claim 1, wherein the movement vector comprises an angular displacement of the user from the first pose to the second pose.

4. The method of claim 1, wherein the movement vector comprises a horizontal translation relative to the vertical gravitational axis of the user from the first pose to the second pose.

5. The method of claim 1, wherein the user has a center of gravity and the vertical gravitational axis intersects the center of gravity of the user along a direction of gravity at the first pose.

6. The method of claim 1, wherein the at least one inertial measurement sensor comprises at least one of a tri-axial accelerometer, a tri-axial magnetometer, or a tri-axial gyroscope.

7. The method of claim 1, wherein the at least one actuator and the inertial measurement sensor are disposed on the band.

8. The method of claim 1, wherein the at least one actuator comprises at least one of an electro-mechanical polymer, a piezo-electric actuator, a solenoid actuator, a pneumatic actuator, a hydraulic actuator, or a linear actuator.

9. The method of claim 1, wherein instructing the at least one actuator to apply the feedback response on the user further comprises:
receiving a video feed of an environment about the user;
augmenting the video feed by adding a stationary virtual object to the video feed, the stationary virtual object indicating the vertical gravitational axis; and
instructing a display of the augmenting video feed on an electronic display in communication with the data processing hardware.

10. The method of claim 1, wherein the feedback response comprises at least one of a force at least partially opposite to and proportional to the movement vector, an audible signal, an emitted light, or a vibration.

11. A wearable comprising:
a band;
actuators disposed on the band, the actuators circumferentially spaced along the band, each actuator configured to apply a force to a user donning the band;
an inertial measurement sensor comprising a tri-axial accelerometer and a tri-axial gyroscope; and
controller in communication with the actuators and the inertial measurement sensor, the controller configured to perform operations comprising:
receiving an inertial measurement from the inertial measurement sensor, the user defining a vertical gravitational axis and a forward travel direction, the user having a pose defined by a sway angle of the user relative to the vertical gravitational axis and a sway direction of the user relative to the forward travel direction, the inertial measurement indicative of a movement of the user from a first pose to a second pose away from the first pose;
determining a movement vector defining the movement of the user from the first pose to the second pose based on the inertial measurement, the movement vector relative to the first pose;
determining whether the movement vector satisfies a threshold movement vector; and
when the movement vector satisfies a threshold movement vector, instructing at least one actuator to apply a force on the user, the force opposite to and proportional to the movement vector.

12. The wearable of claim 11, wherein determining whether the movement vector satisfies a threshold movement vector comprises determining whether the movement vector extends beyond a movement envelope defined by a collection of envelope movement vectors relative to the vertical gravitational axis and the forward travel direction of the user at the first pose.

13. The wearable of claim 11, wherein the movement vector comprises an angular displacement of the user from the first pose to the second pose.

14. The wearable of claim 11, wherein the movement vector comprises a horizontal translation relative to the vertical gravitational axis of the user from the first pose to the second pose.

15. The wearable of claim 11, wherein the user has a center of gravity and the vertical gravitational axis intersects the center of gravity of the user along a direction of gravity at the first pose.

16. The wearable of claim 11, wherein the at least one actuator comprises at least one of a tri-axial accelerometer, a tri-axial magnetometer, or a tri-axial gyroscope.

17. The wearable of claim 11, wherein the inertial measurement sensor is disposed on the band.

18. The wearable of claim 11, wherein the at least one actuator comprises at least one of an electro-mechanical polymer, a piezo-electric actuator, a solenoid actuator, a pneumatic actuator, a hydraulic actuator, or a linear actuator.

19. The wearable of claim 11, wherein the operations further comprise, when the movement vector satisfies a threshold movement vector:
receiving a video feed of an environment about the user;
augmenting the video feed by adding a stationary virtual object to the video feed, the stationary virtual object indicating the vertical gravitational axis; and
causing a display of the augmenting video feed on an electronic display in communication with the controller.

20. The wearable of claim 11, wherein the operations further comprise, when the movement vector satisfies a threshold movement vector, triggering an ancillary feedback response comprising an audible response, a visual response, or a vibratory response.

21. A method comprising:
receiving, at data processing hardware, an inertial measurement from an inertial measurement sensor disposed on a user, the inertial measurement sensor comprising a tri-axial accelerometer and a tri-axial gyroscope, the user defining a vertical gravitational axis and a forward travel direction, the user having a pose defined by a sway angle of the user relative to the vertical gravitational axis and a sway direction of the user relative to the forward travel direction, the inertial measurement indicative of a movement of the user from a first pose to a second pose away from the first pose;
determining, by the data processing hardware, a movement vector defining the movement of the user from the first pose to the second pose based on the inertial measurement, the movement vector relative to the first pose;

determining, by the data processing hardware, whether the movement vector satisfies a threshold movement vector; and when the movement vector satisfies a threshold movement vector;
- receiving a video feed of an environment about the user;
- augmenting the video feed by adding a stationary virtual object to the video feed, the stationary virtual object indicating the vertical gravitational axis; and
- instructing, by the data processing hardware, display of the augmenting video feed on an electronic display.

22. The method of claim 21, wherein determining whether the movement vector satisfies a threshold movement vector comprises determining whether the movement vector extends beyond a movement envelope defined by a collection of envelope movement vectors relative to the vertical gravitational axis and the forward travel direction of the user at the first pose.

23. The method of claim 21, wherein the movement vector comprises an angular displacement of the user from the first pose to the second pose.

24. The method of claim 21, wherein the movement vector comprises a horizontal translation relative to the vertical gravitational axis of the user from the first pose to the second pose.

25. The method of claim 21, wherein the user has a center of gravity and the vertical gravitational axis intersects the center of gravity of the user along a direction of gravity.

26. The method of claim 21, wherein the at least one inertial measurement sensor comprises at least one of a tri-axial accelerometer, a tri-axial magnetometer, or a tri-axial gyroscope.

27. The method of claim 21, wherein the inertial measurement sensor is disposed on a band wearable by the user.

28. The method of claim 21, wherein electronic display comprises a head mounted display.

29. The method of claim 21, further comprising when the movement vector satisfies a threshold movement vector, triggering an ancillary feedback response comprising an audible response, a visual response, or a vibratory response.

* * * * *